(12) United States Patent
Lanza et al.

(10) Patent No.: US 6,676,963 B1
(45) Date of Patent: Jan. 13, 2004

(54) LIGAND-TARGETED EMULSIONS CARRYING BIOACTIVE AGENTS

(75) Inventors: Gregory M. Lanza, St. Louis, MO (US); Samuel A. Wickline, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 150 days.

(21) Appl. No.: 09/697,796

(22) Filed: Oct. 27, 2000

(51) Int. Cl.[7] .......................... A61K 9/127; A61K 9/107
(52) U.S. Cl. ..................... 424/450; 424/1.21; 424/1.37; 424/9.321; 424/9.51; 424/94.3; 514/937
(58) Field of Search .................. 424/450, 9.5, 1.21, 424/1.37, 9.321, 9.51, 417, 94.3; 436/829; 514/937–943

(56) References Cited

U.S. PATENT DOCUMENTS

| | | |
|---|---|---|
| 4,927,623 A | 5/1990 | Long, Jr. |
| 4,987,154 A | 1/1991 | Long, Jr. |
| 5,077,036 A | 12/1991 | Long, Jr. |
| 5,114,703 A | 5/1992 | Wolf et al. |
| 5,171,755 A | 12/1992 | Kaufman et al. |
| 5,304,325 A | 4/1994 | Kaufman et al. |
| 5,310,505 A | 5/1994 | Hedden et al. |
| 5,350,571 A | 9/1994 | Kaufman et al. |
| 5,393,524 A | 2/1995 | Quay |
| 5,401,634 A | 3/1995 | Milbrath |
| 5,403,575 A | 4/1995 | Kaufman et al. |
| 5,542,935 A | 8/1996 | Unger et al. |
| 5,690,907 A | 11/1997 | Lanza et al. |
| 5,780,010 A | 7/1998 | Lanza et al. |
| 5,785,950 A | 7/1998 | Kaufman et al. |
| 5,958,371 A | 9/1999 | Lanza et al. |
| 5,989,520 A | 11/1999 | Lanza et al. |
| 6,120,794 A * | 9/2000 | Liu |

FOREIGN PATENT DOCUMENTS

WO   WO 95/03829   2/1995

OTHER PUBLICATIONS

Leveille–Webster et al., "Enhancement Effects of a Hepatocyte Receptor–Specific MR Contrast Agent in an Animal Model", J. Magn. Reson Imaging, 1994, pp. 325–330, vol. 4.

Wright et al., "Evaluation of New Thrombus–Specific Ultrasound Contrast Agent", Acad. Radiol., 1998, pp. S240–S242, vol. Suppl. 1.

Collins–Gold et al., "Parental Emulsions for Drug Delivery", Advanced Drug Delivery Reviews, 1990, pp. 189–208, vol. 5:3.

Leveille–Webster et al., "Use of an Asialogycoprotein Receptor–Targeted Magnetic Resonance Contrast Agent to Study Changes in Receptor Biology During Liver Regeneration and Endotoxemia in Rats", Hepatology, 1996, pp. 1631–1641, vol. 23:6.

(List continued on next page.)

*Primary Examiner*—Collamudi S. Kishore
(74) *Attorney, Agent, or Firm*—Morrison & Foerster LLP

(57) ABSTRACT

A composition for use in delivering a bioactive agent to targeted tissues or cells comprises: (a) a site-specific targeting ligand; (b) a lipid encapsulated oil in water emulsion; and (c) a bioactive agent in or on the surface of the outer monolayer of the emulsion; the ligand being conjugated directly or indirectly to the emulsion and the composition providing facilitated delivery of the bioactive agent through prolonged association and increased contact of the ligand-bound lipid encapsulated emulsion particles with the lipid bilayer of the target tissues or cells. The composition may also comprise a lipid encapsulated oil in water emulsion and a combination site-specific targeting ligand/bioactive agent. Methods for improved delivery of a bioactive agent to targeted tissues or cells are also disclosed.

60 Claims, 3 Drawing Sheets

OTHER PUBLICATIONS

Leveille–Webster et al., "Enhancement Effects of a Hepatocyte Receptor–Specific MR Contrast Agent in an Animal Model", J. Magn. Reson Imaging, 1994, pp. 325–330, vol. 4.

Reimer et al., "Pancreatic Receptors: Intial Feasibility Studies with a Targeted Contrast Agent for MR Imaging", Radiology, 1994, pp. 527–531, vol. 193:1, USA.

Reimer et al., "Preclinical Assessment of Hepatocyte–Targeted MR Contrast Agents in Stable Human Liver Cell Cultures", Journal of Magnetic Resonance Imaging, 1998, pp. 687–689, vol. 8:3.

Reimer et al., "Dymanic Signal Intensity Changes in Liver with Superparamagnetic MR Contrast Agents", Journal ogf Magnetic Resonance Imaging, 1992, pp. 177–181, vol. 2:2.

Reimer et al., "Receptor–Directed Contrast Agents for MR Imaging: Preclinical Evaluation with Affinity Assays", Radiology, 1992, pp. 565–569, vol. 182:2, USA.

Sche et al., "Display Cloning: Functional Identification of Natural Product Receptors Using cDNA–Phage Display", Chemistry & Biology, 1999, pp. 707–716, vol. 6:10.

Stadler B., "Antibody Production Without Animals", Dev. Biol. Stand. Basel, Karger, 1999, pp. 45–48, vol. 101.

Tarr et al., "A New Parenteral Emulsion for the Administration of Taxol", Pharmaceutical Research, 1987, pp. 162–165, vol. 4:2.

Wittrup K., "Phage on Display", Trends Biotechnol., 1999, pp. 423–424, vol. 17.

Wright et al., "Evaluation of New Thrombus–Specific Ultrasound Contrast Agent", Acad. Radiol., 1998, pp. S240–S242, vol. Suppl. 1.

* cited by examiner

LIGAND-TARGETED EMULSIONS CARRYING BIOACTIVE AGENTS

BACKGROUND OF THE INVENTION

This invention relates to ligand-targeted emulsions that incorporate biologically active agents on or in their particle surface, and more particularly, to such novel emulsions that are especially useful for the treatment of disease with bioactive agents that have improved risk/benefit profiles when applied specifically to selected cells, tissues or organs.

As used herein, the following terms have the definitions set forth:

Direct conjugation of ligand to the emulsion particle refers to the preparation of a ligand-particle complex before administration wherein the ligand is either adsorbed through ionic, electrostatis, hydrophobic or other noncovalent means to the particle surface (e.g. acylated-antibody), or chemically linked to the surface through covalent bonds to a component of the lipid surface such as a "primer material" (e.g. thio-ether or ester bond), or intrinsically incorporated into the lipid surfactant membrane as a component of the membrane (e.g. a lipid derivatized to a peptiodomimetic agent).

Indirect conjugation refers to the use of avidin biotin where the complex is formed in vivo in two or more steps. An example would be giving the biotinylated antibody first, followed by avidin, and followed by the biotinylated emulsion particle. Any other sequential multistep chemical linking system that could be utilized in vivo is envisioned to produce the same end result, i.e. the close and specific apposition of the emulsion particle to a targeted cell or tissue surface.

Primer material refers to any constituent or derivatized constituent incorporated into the emulsion lipid surfactant layer that could be chemically utilized to form a covalent bond between the particle and a targeting ligand or a component of the targeting ligand (if it has subunits).

Prolonged association of the emulsion particle with the surface of the targeted cell or tissue is in contradistinction to the transient interaction that an unbound particle, existing free in extracellular body fluids, would achieve. By binding the particle to the cell surface, the continued circulation of the nanoparticle through the body is halted. The affixed particle is able to interact with the target cell surface over an extended period of time. The exact amount of time may be variable, but is meant to exceed that of more transient nontargeted contact between particles and cell surfaces by orders of magnitude.

Surfactant is a term derived from SURFace ACTive AgeNT. A Surfactant is a compound that contains a hydrophilic and a hydrophobic segment. When added to water or solvents, a surfactant reduces the surface tension of the systems for the following purposes emulsifying or dispersing in the present application. Our preferred surfactants are phospholipids and cholesterol but include those lipids that are mentioned in our previous application and the additional detergents specified in our invention disclosure.

Ligand is a molecule that binds to another molecule, used in this application to refer to a small targeting molecule that binds specifically to another molecule on a biological surface separate and distinct from the emulsion particle itself. The reaction does not require nor exclude a molecule that donates or accepts a pair of electrons to form a coordinate covalent bond with a metal atom of a coordination complex.

Emulsion technology is very old and distinct from the more modern liposome technology. This is exemplified by the prolific research and patent literature involving liposomes since the 1963 report by Bangham (Physical structure and behavior of lipids and lipid enzymes., Adv Lipid Res, 1963; 1:65–104). Bangham originally characterized emulsions as "either temporary or permanent dispersions of oils or hydrophobic material in water or vice versa" and liposomes as " . . . 'myelins' and 'myelinics' . . . irrevocably associated with the structures obtained when certain phospholipids are dispersed in water. . . . The unit structure is a biomolecular tube of lipids, separated from its adjacent concentric tube by a layer of water." In later years liposomes have been elegantly described as "vesicles in which an aqueous volume is entirely enclosed by a membrane composed of lipid molecules . . . (which) form spontaneously when these lipids are dispersed in aqueous media. . . . The liposome membrane forms a bilayer structure which is in principle identical to the lipid portion of natural cell membranes." Liposomes may be prepared by a variety of techniques and have single or multiple membrane layers. They are distinctly different and more complex than emulsions.

Drugs can be incorporated into liposomes within either the internal aqueous phase or within one or more of the lipid bilayer membranes and liposomes can be coupled to ligands of various types. Because of the bilayer nature of a liposome membrane, lipophilic drugs incorporate into both the inner and outer leaflets of the bilayer. Drugs, bound to the inner leaflet layer are unavailable for immediate delivery by contact facilitated delivery as opposed to lipid encapsulated emulsions. For multilamellar liposomes, most of the drug will be internalized within the liposome and not readily available for contact facilitated delivery to a target cell. To extend circulatory half-life, liposomes have been modified with polymerized lipids or the addition of polyethylene glycol to enhance in vivo survivability. Both modifications protect the particles from lipid exchange with other cells and lipoproteins.

"An emulsion is a heterogeneous system, consisting of at least one immiscible liquid intimately dispersed in another in the form of droplets, whose diameters, in general, exceed $0.1\mu$. Such systems possess a minimal stability, which may be accentuated by such additives as surface-active agents, finely-divided solids, etc." (Becher P. Emulsion: Theory and Practice, New York, N.Y.; Reinhold Publishing Corporation; 1965) "The phase which is present in the form of finely divided droplets is called the dispersion or internal phase; the phase which forms the matrix in which these droplets are suspended is called the continuous or external phase . . . Surface active or other agents which are added to increase stability . . . are known as emulsifiers or emulsifying agents. Stability is also increased by mechanical devices such as simple stirrers, homogenizers or colloid mills."

Liquid perfluorocarbon emulsions are specialized formulations with various medical and oxygen transport applications. They are especially useful medically as contrast media, for various biological imaging modalities such as nuclear magnetic resonance, ultrasound, x-ray, computed tomography, F-magnetic resonance imaging, and position emission tomography, as oxygen transport agents or "artificial bloods," in the treatment of heart attack, stroke, and other vascular obstructions, as adjuvants to coronary angioplasty and in cancer radiation treatment and chemotherapy. The fluorocarbon emulsion can be used to deliver drugs and medicines soluble in or transportable by the emulsion.

Long et al. U.S. Pat. No. 4,987,154 discloses that fluorocarbon emulsions can deliver therapeutic agents, medicines and drugs throughout the body, tissue and organs by at least two modes: 1) within the fluorocarbon phase or 2) by complexing of the agent, medicine or drug with the surfactant membrane. Long et al. cite examples of medicines, drugs and therapeutic agents that can be dissolved in the fluorocarbon including diazepam, cyclosporin, rifampin, clindamycin, isoflurane, halothane and enflurane. Examples of medicines, therapeutic agents and drugs that do not dissolve in fluorocarbon, but can be complexed with, for example, a lecithin membrane include mannitol, tocopherol, streptokinase, dexamethasone, prostaglandin E, interleukin, gentamycin and cefoxitin. Antibiotics may be delivered transcutaneously through the skin when added to a fluorocarbon emulsion. Furthermore, proteins such as thrombolytic agents, hormones or enzymes can be transported and delivered by fluorocarbon emulsions.

Delivery of drugs as described by Long et al. and others depend upon the encapsulated drug being more slowly metabolized and eliminated from the circulation than free drug. In other cases, the encapsulated particles are sequestered into organs and cells involved with the normal metabolism and clearance of particles and foreign matter from the body, a process referred to as passive targeted delivery. The opportunity to conjugate ligands to perfluorocarbon emulsions for the purpose of contact facilitated delivery of bioactive agents was not envisioned by Long et al.

We have previously reported a novel ligand-targeted, lipid-encapsulated nongaseous perfluorocarbon emulsion useful for ultrasound, magnetic resonance and nuclear imaging applications (U.S. Pat. Nos. 5,690,907, 5,780,010, 5,958,371 and 5,989,520). The perfluorocarbon emulsion is produced through microfluidization techniques, and is robustly stable to handling, pressure, atmospheric exposure, heat and shear. In the early phases of development, we coupled a pretargeted biotinylated ligand to a biotinylated version of the emulsion nanoparticle through avidin-biotin interactions. Subsequently, we adopted a direct ligand conjugation approach using monoclonal $F_{(ab)}$ fragments to facilitate future clinical implementations.

The emulsion nanoparticles have long circulatory half-lives due to their small size and inherent in vivo stability without further modification of their outer lipid surfaces with polyethylene glycol or incorporation of polymerized lipids. Surfactant modifications often detract from targeting efficacy in order to extend circulatory persistence. The in vivo clearance of the nanoparticles was measured in dogs by quantification of the blood perfluorocarbon content with an estimated half-life of one hour. Preliminary data suggest that this novel agent will persist bound to tissue for hours, and dependent upon location, even days.

Millbrath et al [U.S. Pat. No. 5,401,634] disclose fluorochemical emulsions comprised of a fluorochemical discontinuous phase and aqueous continuous phase with at least one specific binding species immobilized on the droplets. The emulsions can include a "primer material" to couple specific binding species to the fluorochemical droplets. The emulsions may be used in diagnostic procedures or biochemical reactors where binding of the immobilized specific binding species to its binding partner is desired. The droplets were envisioned to incorporate a species (e.g. dye) that is detectable by spectrophotometric, fluorometric or colormetric means. These inventors were focused upon in vitro applications and were unconcerned with in vivo targeted drug delivery. Moreover, they never conceived of the benefits of contact facilitated drug or gene delivery achieved through ligand-targeted emulsion technology.

Magdassi et al, (published PCT application WO 95/03829) described the production and use of ligand-targeted oil emulsions in which drug is "dissolved, dispersed or solubilized inside the oil droplet, creating a novel drug targeting system". The targeted particles provide an oil encapsulated depot of drug at the target site. Subsequent breakdown of the particles releases drug to the interstium. The agent is diluted in extracellular fluids and can migrate from the interstitium to the target cell. Magdassi et al. do not conceive of the utility of contact facilitated delivery of drug or genes from an outer surfactant layer to target tissues. They do not recognize the importance or advantages of a biocompatible phospholipid surfactant layer amenable to exchanging constituents with the target cell membrane. Contact facilitated drug delivery with ligand-targeted emulsions places all of the drug into a monolayer surrounding the particle, ready to interact with the target surface. Mobility of the phospholipid monolayer over the particle surface allows drug from all regions of the layer to migrate and interact with target cell surfaces. Encapsulating drug within the particle, as described by Magdassi et al. isolates the agent from the particle surface and prevents contact facilitated delivery to the target cell membrane.

Unger et al (U.S. Pat. No. 5,542,935) have described therapeutic delivery systems for site-specific delivery of bioactive agents using gas-filled perfluorocarbon microspheres. The microspheres contain a temperature activated gaseous precursor that becomes a gas upon activation at a selected temperature. Once the microspheres have been introduced into the patient's body, a therapeutic compound may be targeted to specific tissues through the use of sonic energy, microwave energy, magnetic energy, or hyperthermia, which is directed to the target area and causes the microspheres to rupture and release the therapeutic compound. Perfluorocarbons preferred include perfluoromethane, perfluoroethane, perfluorobutane, perfluoropentane, perfluorohexane; even more preferably perfluoroethane, perfluoropentane, perfluoropropane, and perfluorobutane. Unger et al. notes that the localization of these particles for cavitation can be improved with conjugated ligand and the process of active targeting.

There remains a need for improved bioactive agent delivery systems which provide enhanced efficiency of such bioactive agents to targeted tissues, cells or organs.

SUMMARY OF THE INVENTION

Among the several objects of the invention may be noted the provision of novel compositions and methods for use in delivering bioactive agents to targeted tissues or cells; the provision of such compositions which provide enhanced delivery of bioactive agents to targeted tissues or cells; the provision of such methods which provides enhanced intermingling and exchange of lipid components from one lipid surface to the other thereby facilitating the exchange of bioactive agents within or on the bioactive agent/emulsion surface to the target cells or tissues; and the provision of such compositions and methods which may be readily practiced. Other objects will be in part apparent and in part pointed out hereinafter.

Briefly, in one aspect, the present invention is directed to a composition for use in delivering a bioactive agent to targeted tissues or cells comprising:

(a) site-specific targeting ligand;

(b) a lipid encapsulated oil in water emulsion; and (c) a bioactive agent in or on the surface of the outer lipid monolayer of said emulsion, said ligand being conjugated directly or indirectly to said emulsion and the composition providing facilitated delivery of the bioactive agent through prolonged association and increased contact of the ligand-bound, lipid encapsulated emulsion particles with the lipid bilayer of said target tissues or cells. The invention is also directed to a method for improved delivery of a bioactive agent to targeted tissues or cells comprising administering the above-noted compositions to said tissues or cells.

DESCRIPTION OF THE PREFERRED EMBODIMENTS

Figure 1:
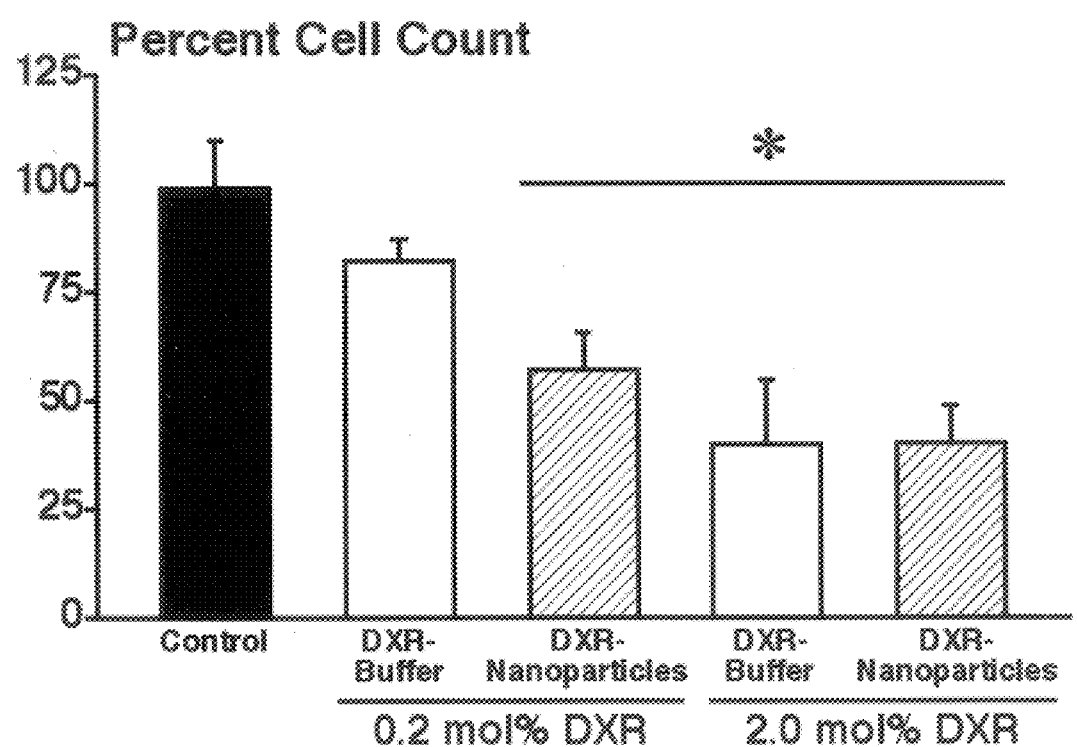
FIG. 1 is a graph showing that tissue factor-targeted doxorubicin (DXR) nanoparticles had greater antiproliferative effects than free doxorubicin and that this differential effect was greater at the lower dosage of doxorubicin.

In accordance with the present invention, it has now been found that improved compositions for use in delivering a bioactive agent to targeted tissues or cells may be formulated by combining (a) a site-specific targeting ligand; (b) a lipid encapsulated oil in water emulsion; and (c) a bioactive agent in or on the surface of the outer lipid monolayer of the emulsion. The present invention thus relates to ligand-targeted emulsions that incorporate biologically active agents on or in the outer monolayer of the lipid-based emulsion particle surface. These novel emulsions are particularly useful for the treatment of disease with biological agents that have improved risk/benefit profiles when applied specifically to selected cells, tissues or organs. Site-directed, lipid encapsulated emulsions provide a unique opportunity to deliver potent bioactive agents, such as chemotherapeutic agents, nucleic acid-based therapy, protein-or peptide therapy and the like, with enhanced efficiency to targeted tissues through a unique form of bioactive agent transfer into target cells, i.e. contact facilitated delivery. Contact facilitated delivery of bioactive agents by targeted lipid encapsulated emulsions reflects the prolonged association and increased contact of the ligand-bound, lipid-encapsulated particles with the lipid bilayer of the target cell. Enhanced intermingling and exchange of lipid components from one lipid surface to the other facilitates the exchange of bioactive agents within or on the therapeutic emulsion surface to the target cell. It will be understood that the bioactive agent is in or on the surface of the outer lipid monolayer of the emulsion and is preferably, in accordance with the invention, not carried or deposited in the interior of the emulsion particles. It will also be understood that in accordance with the present invention, the emulsion must be nongaseous, i.e. should be a liquid emulsion.

Prolonged association of the emulsion particles with the surface of the targeted cell or tissue is in contradistinction to the transient interaction that an unbound particle, existing free in extracellular body fluids, would achieve. By binding the particle to the cell surface, the continued circulation of the nanoparticle through the body is halted. The affixed particle is able to interact with the target cell surface over an extended period of time. The exact amount of time may be variable, but is meant to exceed that of more transient nontargeted contact between particles and cell surfaces by orders of magnitude.

Targeted therapeutic emulsion may be delivered and concentrated at desired sites in vivo using active-targeting techniques. Active targeting refers to ligand-directed, site-specific accumulation of agents to cells, tissues or organs by localization and binding to molecular epitopes, ie, receptors, lipids, peptides, cell adhesion molecules, polysaccharides, biopolymers, and the like, presented on the surface membranes of cells or within the extracellular matrix. A wide variety of ligands, including but not limited to antibodies, antibody fragments, peptides, small molecules, polysaccharides, nucleic acids, aptamers, peptidomimetics, other mimetics and drugs alone or in combination may be utilized to specifically bind to cellular epitopes and receptors. These ligands may be attached covalently (direct-conjugation) or noncovalently (indirect conjugation) to the acoustic particle surface.

Avidin-biotin interactions are extremely useful, noncovalent targeting systems that have been incorporated into many biological and analytical systems and selected in vivo applications. Avidin has a high affinity for biotin ($10^{-15}$M) facilitating rapid and stable binding under physiological conditions. Targeted systems utilizing this approach are administered in two or three steps, depending on the formulation. Typically, a biotinylated ligand, such as a monoclonal antibody, is administered first and "pretargeted" to the unique molecular epitopes. Next, avidin is administered, which binds to the biotin moiety of the "pretargeted" ligand. Finally, the biotinylated agent is added and binds to the unoccupied biotin-binding sites remaining on the avidin thereby completing the ligand-avidin-emulsion "sandwich". The avidin-biotin approach can avoid accelerated, premature clearance of targeted agents by the MPS system secondary to the presence of surface antibody. Additionally, avidin, with four, independent biotin binding sites provides signal amplification and improves detection sensitivity.

Targeting ligands may be chemically attached to the surface of acoustic or emulsion particles by a variety of methods depending upon the nature of the ligand and composition of the particle surface. A ligand is a molecule that binds to another molecule, and as used in this application refers to a small targeting molecule that binds specifically to another molecule on a biological surface separate and distinct from the emulsion particle itself. The reaction does not require nor exclude a molecule that donates or accepts a pair of electrons to form a coordinate covalent bond with a metal atom of a coordination complex. Conjugations may be performed before or after the emulsion particle is created depending upon the ligand employed. Direct chemical conjugation of ligands to proteinaceous agents often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for ligand conjugation after the particles are formed. Another common post-processing approach is to activate surface carboxylates with carbodiimide prior to ligand addition. The selected covalent linking strategy is primarily determined by the chemical nature of the ligand. Monoclonal antibodies and other large proteins may denature under harsh processing conditions; whereas, the bioactivity of carbohydrates, short peptides, aptamers, drugs or peptidomimetics often can be preserved. To ensure high ligand binding integrity and maximize targeted particle avidity flexible polymer spacer arms, e.g. polyethylene glycol, amino acids or simple caproate bridges, can be inserted between an activated surface functional group and the targeting ligand. These extensions can be 10 nm or longer and minimize interference of ligand binding by particle surface interactions.

Monoclonal Antibody and Fragments

Rapid expansion of the monoclonal antibody industry has prepared the stage for the clinical success of site-targeted agents by providing a plethora of ligands that can be directed against a wide spectrum of pathologic molecular epitopes. Antibodies or their fragments may be from several classes including IgG, IgM, IgA, IgE or IgD. Immunoglobin-γ (IgG) class monoclonal antibodies have been most often conjugated to liposomes, emulsions and other microbubble particles to provide active, site-specific targeting. These proteins are symmetric glycoproteins (MW ca. 150,000 daltons) composed of identical pairs of heavy and light chains. Hypervariable regions at the end of each of two arms provide identical antigen-binding domains. A variably sized branched carbohydrate domain is attached to complement-activating regions, and the hinge area contains particularly accessible interchain disulfide bonds that may be reduced to produce smaller fragments.

Bivalent F(ab')$_2$ and monovalent F(ab) fragments are derived from selective cleavage of the whole antibody by pepsin or papain digestion, respectively. Elimination of the Fc region greatly diminishes the immunogenicity of the molecule, diminishes nonspecific liver uptake secondary to bound carbohydrate, and reduces complement activation and resultant antibody-dependent cellular toxicity. Complement fixation and associated cellular cytotoxicity can be detrimental when the targeted site must be preserved or beneficial when recruitment of host killer cells and target-cell destruction is desired (e.g. anti-tumor agents).

Most monoclonal antibodies are of murine origin and are inherently immunogenic to varying extents in other species. Humanization of murine antibodies through genetic engineering or other combinatorial chemical methods have led to development of chimeric ligands with improved biocompatibility and longer circulatory half-lives. The binding affinity of recombinant antibodies to targeted molecular epitopes can be occasionally improved with selective site-directed mutagenesis of the binding idiotype.

Phage Display

Phage display techniques are now used to produce recombinant human monoclonal antibody fragments against a large range of different antigens without involving antibody-producing animals. In general, cloning creates large genetic libraries of corresponding DNA (CDNA) chains deducted and synthesized by means of the enzyme "reverse transcriptase" from total messenger RNA (mRNA) of human B lymphocytes. Immunoglobulin cDNA chains are amplified by PCR (polymerase chain reaction) and light and heavy chains specific for a given antigen are introduced into a phagemid vector. Transfection of this phagemid vector into the appropriate bacteria results in the expression of a scFv immunoglobulin molecule on the surface of the bacteriophage. Bacteriophages expressing specific immunoglobulin are selected by repeated immunoadsorption/phage multiplication cycles against desired antigens (e.g., proteins, peptides, nuclear acids, and sugars). Bacteriophages strictly specific to the target antigen are introduced into an appropriate vector, (e.g., *Escherichia coli*, yeast, cells) and amplified by fermentation to produce large amounts of human antibody fragments with structures very similar to natural antibodies. Although this technology is still in early stages of development, it has already permitted the production of unique ligands for targeting and therapeutic applications. (de Bruin et al., Selection of high-affinity phage antibodies from pahage display libraries. Nat Biotechnol. 1999; 17:397–399; Stadler, Antibody production without animals. Dev Biol Stand. 1999; 101:45–48; Wittrup, Phage on display, Trends Biotechnol. 1999; 17:423–424; Sche et al., Display cloning: functional identification of natural product receptors using cDNA-phage display. Chem Biol. 1999; 6:(707–716).

Peptides

Peptides, like antibodies, may have high specificity and epitope affinity for use as vector molecules for targeted contrast agents. These may be small peptides (5 to 10 amino acids) specific for a unique receptor sequences (e.g. such as the RGD epitope of the platelet GIIbIIIa receptor) (Wright et al., Evaluation of New thrombus-specific ultrasound contrast agents. Acad Radiol. 1998; 5 (Supp 1): S240–S242) or larger, biologically active hormones such as cholecystokinin (Reimer et al., Pancreatic receptors: initial feasibility studies with a targeted contrast agent for MR imaging; Radiology, 1994; 193:527–531). Smaller peptides potentially have less inherent immunogenicity than nonhumanized murine antibodies. Peptides or peptide (nonpeptide) analogues of cell adhesion molecules, cytokines, selectins, cadhedrins, Ig superfamily, integrins and the like may be utilized for targeted therapeutic delivery.

Asialoglycoproteins and Polysaccharides

Asialoglycoproteins (ASG) have been used for liver-specific applications due to their high affinity for ASG receptors located uniquely on hepatocytes (Reimer et al., Preclinical assessment of hepatocyte-targeted MR constrast agents in stable human liver cell cultures, J Magn Reson Imaging, 1998; 8:687–698 and Leveille-Webster et al., Use of an asialoglycoprotein receptor-targeted magnetic resonance agent to study changes in receptor biology during liver regeneration and endotoxemia in rats., Hepatology 1996; 23:1631–1641). ASG directed agents (primarily MR agents conjugated to iron oxides) have been used to detect primary and secondary hepatic tumors as well as benign, diffuse liver disease such as hepatitis (Reimer et al., Dynamic signal intensity changes in liver with superparamagnetic MR constrast agents., J Magn Reson Imaging, 1992; 2:177–181 and Reimer et al., Receptor-directed contrast agents for MR imaging preclinical evaluation with affinity assays., Radiology, 1992; 182:565–569). The ASG receptor is highly abundant on hepatocytes, approximately 500,000 per cell, rapidly internalizes and is subsequently recycled to the cell surface. Polysaccharides such as arabinogalactan may also be utilized to localize agents to hepatic targets. Arabinogalactan has multiple terminal arabinose groups that display high affinity for ASG hepatic receptors (Leveille-Webster et al., supra and Small et al., Enhancement effects of a hepatocyte receptor-specific MR contrast agent in an animal model., J Magn Reson Imaging, 1994; 4:325–330).

Aptamers

Aptamers are high affinity, high specificity RNA or DNA-based ligands produced by in vitro selection experiments (SELEX: systematic evolution of ligands by exponential enrichment) (Small et al., supra).

Aptamers are generated from random sequences of 20 to 30 nucleotides, selectively screened by absorption to molecular antigens or cells, and enriched to purify specific high affinity binding ligands. To enhance in vivo stability and utility, aptamers are generally chemically modified to impair nuclease digestion and to facilitate conjugation with drugs, labels or particles. Other, simpler chemical bridges often substitute nucleic acids not specifically involved in the ligand interaction. In solution aptamers are unstructured but can fold and enwrap target epitopes providing specific recognition. The unique folding of the nucleic acids around the epitope affords discriminatory intermolecular contacts through hydrogen bonding, electrostatic interaction, stacking, and shape complementarity. In comparison with protein-based ligands, aptamers are stable, are more conducive to heat sterilization, and have lower immunogenicity. Aptamers are currently used to target a number of clinically relevant pathologies including angiogenesis, activated platelets, and solid tumors and their use is increasing. The clinical effectiveness of aptamers as targeting ligands for therapeutic emulsion particles may be dependent upon the impact of the negative surface charge imparted by nucleic acid phosphate groups on clearance rates. Previous research with lipid-based particles suggest that negative zeta potentials markedly decrease liposome circulatory half-life, whereas, neutral or cationic particles have similar, longer systemic persistence.

The oil phase of the oil in water emulsion may be a vegetable oil, medium chain triglycerides (MCT) or any other oil, with increased or decreased polarity and hydrophobicity or fluorochemical liquid. Suitable fluorochemical liquids include straight and branched chain and cyclic perfluorocarbons, straight and branched chain and cyclic perfluoro tertiary amines, straight and branched chain and cyclic perfluoro ethers and thioethers, halofluorocarbons and polymeric perfluoro ethers and the like. Although up to 50% hydrogen-substituted compounds can be used, perhalo compounds are preferred. Most preferred are perfluorinated compounds.

Although any fluorochemical liquid i.e. a substance which is a liquid at about 20 degree.C. at atmospheric pressure, can be used to prepare a fluorochemical emulsion of the present invention, for many purposes emulsions with longer extended stability are preferred. In order to obtain such emulsions, fluorochemical liquids with boiling points above 30.degree. C. are preferred. Preferably the fluorochemical liquids have boiling points above 50° C., and most preferred are fluorochemical liquids with boiling points above about 90° C.

Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorodecalin, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds and are partially or fully halogenated (including at least some fluorine substituents) or partially or fully perfluorinated including perfluoroalkylated ether, polyether or crown ether.

Emulsifying agents, for example surfactants, may be used to facilitate the formation of emulsions. Typically, aqueous phase surfactants have been used to facilitate the formation of emulsions of fluorochemical liquids. A variety of lipid surfactants may be incorporated into the lipid monolayer preferably natural or synthetic phospholipids, but also fatty acids, cholesterols, lysolipids, sphingomyelins, tocopherols, glucolipids, stearylamines, cardiolipins, a lipid with ether or ester linked fatty acids, polymerized lipids, and lipid conjugated polyethylene glycol. The preferred surfactants for use in the practice of the invention are phospholipids and cholesterol. Other known surfactants such as Pluronic F-68, Hamposyl.TM. L30 (W. R. Grace Co., Nashua, N.H.), sodium dodecyl sulfate, Aerosol 413 (American Cyanamid Co., Wayne, N.J.), Aerosol 200 (American Cyanamid Co.), Lipoproteol.TM. LCO (Rhodia Inc., Mammoth, N.J.), Standapol.TM. SH 135 (Henkel Corp., Teaneck, N.J.), Fizul.TM. 10–127 (Finetex Inc., Elmwood Park, N.J.), and Cyclopol.TM. SBFA 30 (Cyclo Chemicals Corp., Miami, Fla.); amphoterics, such as those sold with the trade names: Deriphat.TM. 170 (Henkel Corp.), Lonzaine.TM. JS (Lonza, Inc.), Niranol.TM. C2N-SF (Miranol Chemical Co., Inc., Dayton, N.J.), Amphoterge.TM. W2 (Lonza, Inc.), and Amphoterge.TM. 2WAS (Lonza, Inc.); non-ionics, such as those sold with the trade names: Pluronic.TM. F-68 (BASF Wyandotte, Wyandotte, Mich.), Pluronic.TM. F-127 (BASF Wyandotte), Brij.TM. 35 (ICI Americas; Wilmington, Del.), Triton.TM. X-100 (Rohm and Haas Co., Philadelphia, Pa.), Brij.TM. 52 (ICI Americas), Span.TM. 20 (ICI Americas), Generol.TM. 122 ES (Henkel Corp.), Triton.TM. N-42 (Rohm and Haas Co.,), Triton.TM. N-101 (Rohm and Haas Co.,), Triton.TM. X-405 (Rohm and Haas Co.,), Tween.TM. 80 (ICI Americas), Tween.TM. 85 (ICI Americas), and Brij.TM. 56 (ICI Americas) and the like may be used. These surfactants' are used alone or in combination in amounts of 0.10 to 5.0% by weight to assist in stabilizing the emulsions.

Fluorinated surfactants which are soluble in the fluorochemical liquid to be emulsified can also be used. Suitable fluorochemical surfactants include perfluorinated alkanoic acids such as perfluorohexanoic and perfluorooctanoic acids and amidoamine derivatives. These surfactants are generally used in amounts of 0.01 to 5.0% by weight, and preferably in amounts of 0.1 to 1.0%. Other suitable fluorochemical surfactants include perfluorinated alcohol phosphate esters and their salts; perfluorinated sulfonamide alcohol phosphate esters and their salts; perfluorinated alkyl sulfonamide alkylene quaternary ammonium salts; N,N-(carboxyl-substituted lower alkyl) perfluorinated alkyl sulfonamides; and mixtures thereof. As used herein, the term "perfluorinated" means that the surfactant contains at least one perfluorinated alkyl group.

Suitable perfluorinated alcohol phosphate esters include the free acids of the diethanolamine salts of mono- and bis(1H,1H,2H,2H-perfluoroalkyl)phosphates. The phosphate salts, available under the tradename "Zonyl RP" (E. I. Dupont de Nemours and Co., Wilmington, Del.), are converted to the corresponding free acids by known methods. Suitable perfluorinated sulfonamide alcohol phosphate esters are described in U.S. Pat. No. 3,094,547. Suitable perfluorinated sulfonamide alcohol phosphate esters and salts of these include perfluoro-n-octyl-N-ethylsulfonamidoethyl phosphate, bis(perfluoro-n-octyl-N-ethylsulfonamidoethyl)phosphate, the ammonium salt of bis(perfluoro-n-octyl-N-ethylsulfonamidoethyl)phosphate, bis(perfluorodecyl-N-ethylsulfonamidoethyl)-phosphate and bis(perfluorohexyl-N ethylsulfonamidoethyl)-phosphate. The preferred formulations use phosphatidylcholine, derivatized-phosphatidylethanolamine and cholesterol as the aqueous surfactant.

Lipid encapsulated emulsions can be formulated with cationic lipids in the surfactant layer that facilitate the adhesion of nucleic acid material to particle surfaces. Cationic lipids may include but are not limited to DOTMA, N-[1-(2,3-dioleoyloxy)propyl]-N,N,N-trimethylammonium chloride; DOTAP, 1,2-dioleoyloxy-3-(trimethylammonio) propane; DOTB,1,2-dioleoyl-3-(4'-trimethyl-ammonio) butanoyl-sn-glycerol, 1,2-diacyl-3-trimethylammonium-propane; 1,2-diacyl-3-dimethylammonium-propane; 1,2- diacyl-sn-glycerol-3-ethyl phosphocholine; and 3β-[N',N'-dimethylaminoethane)-carbamol]cholesterol-HCl may be used. In general the molar ratio of cationic lipid to non-cationic lipid in the lipid surfactant monolayer may be, for example, 1:1000 to 2:1, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid component of the emulsion surfactant, particularly dipalmitoylphosphatidylcholine, dipalmitoylphosphatidylethanolamine, 1,2-diacyl-sn-glycerol-3-phosphoethanolamine, cholesterol or dioleoylphosphatidylethanolamine in addition to those previously described. In lieu of cationic lipids as described above, lipids bearing cationic polymers such as polylysine or polyarginine may also be included in the lipid surfactant and afford binding of a negatively charged therapeutic, such as genetic material or analogues there of, to the outside of the emulsion particles.

Release of nucleic acid constructs from cationic lipid emulsions can be induced by the incorporation of anionic lipids from adjacent lipid monolayers and faciliated by the prolonged contact and interactions afforded by ligand-targeted emulsions. A similar phenomena has been reported when nucleic acid linked cationic liposomes become intracellular. These anionic lipids form a charged ion-pair with the cationic lipids leading to the displacement of oligonucleotide into the surrounding medium. Delivery of genetic material adsorbed onto the surface of cationic emulsions can be enhanced by ligand-targeted emulsions and contact facilitated delivery. Increased interaction and exchange of lipids from the target cell surface to the outer membrane of the therapeutic particle will facilitate the transfer and release of oligonucleotide.

In accordance with the present invention, the site-specific targeting ligand may be directly or indirectly conjugated to the surface of the emulsion particles. Direct conjugation of ligand to the emulsion particles refers to the preparation of a ligand-particle complex before administration to a patient wherein the ligand is either adsorbed through ionic, electrostatic, hydrophobic or other noncovalent means to the particle surface (e.g. acylated-antibody), or chemically linked to the surface through covalent bonds to a component of the lipid surface such as a"primer material" (e.g. thioether or ester bond), or intrinsically incorporated into the lipid surfactant membrane as a component of the membrane (e.g. a lipid derivatized to a peptidomimetic agent).

Indirect conjugation refers to the use of avidin biotin wherein the complex is formed in vivo in two or more steps. For example, by administering the biotinylated antibody first, followed by avidin, and followed by the biotinylated emulsion particle. Any other sequential multistep chemical linking system that could be used in vivo is envisioned to produce the same end result, i.e. the close and specific apposition of the emulsion particle to a targeted cell or tissue surface.

The emulsions of the present invention may be prepared by various techniques. One method is sonication of a mixture of oil or fluorochemical liquid and an aqueous solution containing a suitable "primer" material and/or specific binding species. Generally, these mixtures include a surfactant. Cooling the mixture being emulsified, minimizing the concentration of surfactant, and buffering with a saline buffer will typically maximize both retention of specific binding properties and the coupling capacity of the primer material. These techniques provide excellent emulsions with high activity per unit of absorbed primer material or specific binding species.

When high concentrations of a primer material or specific binding species coated on lipid emulsions, the mixture should be heated during sonication and have a relatively low ionic strength and moderate to low pH. Too low an ionic strength, too low a pH or too much heat may cause some degradation or loss of all of the useful binding properties of the specific binding species or the coupling capacity of the "primer" material. Careful control and variation of the emulsification conditions can optimize the properties of the "primer" material or the specific binding species while obtaining high concentrations of coating.

Carbohydrate-bearing lipids may be employed for in vivo targeting, as described in U.S. Pat. No. 4,310,505, the disclosures of which are hereby incorporated herein by reference, in their entirety.

While preparation of emulsions by sonication has been acceptable, some degree of variability in particle size distribution may be observed. An alternative method of making the emulsions involves directing high pressure streams of mixtures containing the aqueous solution, a "primer" material or the specific binding species, the oil or fluorocarbon liquid and a surfactant (if any) so that they impact one another to produce emulsions of narrow particle size and distribution. The Microfluidizer™ apparatus (Microfluidics, Newton, Mass.) can be used to make the preferred emulsions. The apparatus is also useful to post-process emulsions made by sonication or other conventional methods. Feeding a stream of emulsion droplets through the Microfluidizer™ apparatus yields formulations of small size and narrow particle size distribution.

Emulsifying and/or solubilizing agents may also be used in conjunction with emulsions. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be used with emulsions include, but are not limited to, acacia, agar, alginic acid, aluminum mono-stearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

Useful emulsions may have a wide range of nominal particle diameters, e.g., from as small as 0.01 microns to as large as 10 microns, preferably 0.1 to 0.5 micron diameter. The emulsion particle sizes can be controlled and varied by modifications of the emulsification techniques and the chemical components.

The specific binding species (i.e. targeting ligand) may be immobilized on the encapsulating lipid monolayer by direct adsorption to the oil/aqueous interface or using a "primer material". A "primer material" is any surfactant compatible compound incorporated in the particle to chemically couple with or adsorb a specific binding or targeting species i.e. any constituent or derivatized constituent incorporated into the emulsion lipid surfactant layer that could be chemically utilized to form a covalent bond between the particle and targeting ligand or a component of the targeting ligand (if it has subunits). The preferred result is achieved by forming an emulsion with an aqueous continuous phase and a biologically active ligand adsorbed or conjugated to the "primer material" at the interface of the continuous and discontinuous phases. Naturally occurring or synthetic polymers with amine, carboxyl, mercapto, or other functional groups capable of specific reaction with coupling agents and highly charged polymers may be utilized in the coupling process. The specific binding species (e.g. antibody) may be immobilized on the emulsion particle surface by direct adsorption or by chemical coupling. Examples of specific binding species which can be immobilized by direct adsorption include small peptides, peptidomimetics, or polysaccharide-based agents. To make such an emulsion the specific binding species may be suspended or dissolved in the aqueous phase prior to formation of the emulsion. Alternatively, the specific binding species may be added after formation of the emulsion and incubated with gentle agitation at room temperature (25° C.) in a pH 7.0 buffer (typically phosphate buffered saline) for 1.2 to 18 hours.

Where the specific binding species is to be coupled to a "primer material", conventional coupling techniques may be used. The specific binding species may be covalently bonded to "primer material" with coupling agents using methods which are known in the art. One type of coupling agent uses a carbodiimide such as 1-ethyl-3-(3-N,N dimethylaminopropyl)carbodiimide hydrochloride or 1-cyclohexyl-3-(2-morpholinoethyl)carbodiimide methyl-p-toluenesulfonate. The priimer material may be phosphatidylethanolamine, N-caproylamine phosphatidylethanolarnine, N-dodecanylamine phosphatidylethanolamine, phosphotidylthioethanol, 1,2-diacyl-sn-glycerol-3-phosphoethanolamine-N-[4-p-maleimidephenyl)-butyramide, N-succinyl-phosphatidylethanolamine, N-glutaryl-phosphatidylethanolamine, N-dodecanyl-phosphatidylethanolamine, N-biotinyl-phosphatidylethanolamine, N-biotinylcaproyl-phosphatidylethanolamine, and phosphatidylethylene glycol. Other suitable coupling agents include aldehyde coupling agents having either ethylenic unsaturation such as acrolein, methacrolein, or 2-butenal, or having a plurality of aldehyde groups such as glutaraldehyde, propanedial or butanedial. Other coupling agents include 2-iminothiolane hydrochloride, bifunctional N-hydroxysuccinimide esters such as disuccinimidyl subsrate, disuccinimidyl tartrate, bis[2-(succinimidooxycarbonyloxy)ethyl]sulfone, disuccinimidyl propionate, ethylene glycolbis(succinimidyl succinate); heterobifunctional reagents such as N-(5-azido-2-nitrobenzoyloxy)succinimide, p-azidophenylbromide, p-azidophenylglyoxal,4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, N-(4-azidophenylthio)phthalamide; homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Covalent bonding of a specific binding species to the "primer material" can be carried out with the above reagents by conventional, well-known reactions, for example, in the aqueous solutions at a neutral pH, at temperatures of less than 25° C. for 1 hour to overnight.

Targeted therapeutic emulsions may incorporate bioactive agents (e.g. drugs, genetic materials, radioactive isotopes, or combinations thereof) in their native form or derivatized with hydrophobic or charged moieties to enhance incorporation or adsorption to the ligand targeted particle. Such therapeutics may include, but are not limited to antineoplastic agents, such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxenes, rapamycin, manumycin A, TNP-470, plicamycin (mithramycin), aminoglutethimide,estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon .alpha.-2a, interferon .alpha.-2b, teniposide (VM-26), vinblastine sulfate (VLB), vincristine sulfate, bleomycin sulfate, hydroxyurea,procarbazine, and dacarbazine; mitotic inhibitors such as etoposide, colchicine, and the vinca alkaloids, radiopharmaceuticals such as radioactive iodine and phosphorus products; hormones such as androgens, progestins, estrogens and antiestrogens; anti-helmintics, antimalarials, and antituberculosis drugs; biologicals such as immune serums, antitoxins and antivenoms; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and .beta.-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and .alpha.-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antitubercurals such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT, DDI, Foscarnet, or Zidovudine), ribavirin and vidarabine monohydrate (adenine arabinoside, ara-A); antianginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine,hydroxychloroquine, metronidazole, quinine and meglumine antimonate; antirheumatics such as penicillamine; narcotics such as paregoric;opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

In addition, the ligand itself, such as an antibody, peptide fragment, or a mimetic of a biologically active ligand may contribute to the inherent therapeutic effects, either as an antagonistic or agonistic, when bound to specific epitopes. As an example, antibody against $\alpha v \beta 3$ integrin on neovascular endothelial cells has been shown to transiently inhibit growth and metastasis of solid tumors. The efficacy of therapeutic emulsion particles directed to the $\alpha v \beta 3$ integrin may result from the improved antagonistic action of the targeting ligand in addition to the effect of the therapeutic agents incorporated and delivered by particle itself. Thus, in another embodiment of the invention, the targeting ligand and bioactive agent may be constituted by a single component which functions both to target the ligand and to provide the bioactive agent to the desired site. As in the other embodiments previously described, when the targeting ligand and bioactive agent are constituted by a single component, such component must still be on or in the surface of the outer monolayer of the lipid encapsulated oil in water emulsion.

The following non-limiting examples illustrate the practice of the invention and the use of the lipid encapsulated oil in water emulsions with bioactive agents which are difficult to administer. By way of background for the examples set forth below, many potent pharmaceutical agents are difficult to administer systemically to patients in a safe and efficacious manner either because of secondary complications due to toxicity of the parent drug or the formulation excipients. Many of these drugs are inherently hydrophobic, such as paclitaxel and analogues thereof. Other compounds are water soluble with lipophilic regions in the parent drug (e.g. doxorubicin) or are amenable to the addition of lipophilic moieties. In this disclosure, we reveal the enhanced effectiveness of such drugs incorporated into or on the surfactant surface of emulsions, such as perfluorocarbon emulsions, targeted specifically to tissues, organs or cells through contact facilitated delivery.

Doxorubicin, is a antineoplastic agent that is incorporated into the treatment regimens of a wide variety of human tumors. Daunorubicin and its 14-hydroxy derivative, doxorubicin, are anthracycline antibiotics produced by the fungus streptomyces peucetius. Doxorubicin is highly water soluble and structurally consists of an aglycon, adriamycinone, combined with an aminosugar, daunosamine Doxorubicin damages DNA by intercalation of the anthracycline portion, metal ion chelation, or by generation of free radicals. Doxorubicin has also been shown to inhibit DNA topoisomerase II which is critical to DNA function. Cytotoxic activity is cell cycle phase-nonspecific. The therapeutic activity of doxorubicin is well validated, and equally well known are its adverse effects, including hair loss, mouth sores, nausea, vomiting, lowered blood counts (WBCs, RBCs and platelets), cardiotoxicity and skin damage secondary to extravasation during intravenous infusion. The anthracycline aspect of the molecule promotes the interaction of doxorubicin with acyl regions of lipid monolayers and bilayers, moderately with neutral layers and strongly with positive or negatively charged membranes hydrophobic and electrostatic interactions. Doxorubicin has been encapsulated into liposomes with demonstrable improvements in organ distribution and effectiveness of the drug as well as a decrease of its cardiotoxicity versus free doxorubicin. The overall benefits of a variety of liposomal doxorubicin versus free drug independent of vesicle composition or formulation process are to decrease systemic toxicity symptoms associated with high peak concentrations of drug and to prolong the pharmacological half-life of the compound.

In addition to liposomal Doxil, doxorubicin and its conjourners have been incorporated into a variety of emulsions and polymeric constructs with some success. Like the liposomal formulations, these formulations strive to administer high payloads of drug with diminished peak concentrations and prolonged systemic half-life. For example, doxorubicin has been prepared as micelles composed of poly(ethylene glycol)-poly(beta-benzyl-L-aspartate) block copolymer (PEG-PBLA) by an o/w emulsion method with a substantial drug loading level (15 to 20 w/w %). Doxorubicin was chemically conjugated to a terminal end group of poly(D, L-lactic-co-glycolic acid) [PLGA] and the doxorubicin-PLGA conjugate was formulated into nanoparticles to sustain the release of doxorubicin. Using sonication and a detergent, iodinated poppy seed oil (IPSO) has been mixed with aqueous solution epirubicin to yield a water-in-oil emulsion that is passed through a microporous glass membrane into saline water-in-oil-in-water emulsion (W/O/W) that consists of IPSO microdroplets. A doxorubicin suspension has been prepared by emulsifying an aqueous solution directly into the lipid contrast medium, Lipiodol.

Another important antineoplastic agent is paclitaxel (i.e. taxol), a member of the class of compounds known as taxines, comes from the bark of the Pacific yew tree, *Taxus brevifolia*. For example, taxol has been used in treating ovarian, breast, non-small cell lung, and head and neck carcinomas. One of the difficulties in administering taxol is that the drug is insoluble in water. The present state of the art in taxol formulation requires a 50:50 mixture of Cremophor-EL surfactant (polyoxyethylated castor oil) and ethanol in order to solubilize the drug. Unfortunately, this taxol formulation leads to a relatively high incidence of major hypersensitivity reactions (HSRs) upon intravenous administration. These HSRs have been attributed to the unusually high concentration of Cremophor-EL required to solubilize the taxol.

There have been other attempts to provide a taxol formulation, the most successful of which has been incorporation of the drug into a liposomal formulation that must be freeze dried and reconstituted prior to use.

Attempts to formulate taxol in a stable lipid emulsion have been unsuccessful. Taxol is reported to be insoluble in lipid emulsions such as Intralipid.RTM., which contains soybean oil, or Liposyn.RTM., which contains a mixture of soybean and safflower oils. L. C. Collins-Gold et al., "Parenteral Emulsions for Drug Delivery", Advanced Drug Delivery Reviews, 5, pp. 189–208 (1990). Heating taxol in either soybean oil or safflower oil, even upon sonication, does not result in the dissolution of appreciable amounts of taxol, and addition of taxol to a lipid emulsion during the homogenization step meets with equally disappointing results. Emulsions incorporating up to 15 mg/ml of taxol have been formulated with triacetin, L-.alpha.-lecithin, Polysorbate 80, Pluronic F-68, ethyloleate and glycerol. However, these emulsions are highly toxic and unstable. B. Tarr et al., "A New Parenteral Emulsion for the Administration of Taxol", Pharmaceutical Research, 4, pp. 162–165 (1987).

Kaufman et al (U.S. Pat. No. 5,785,950) have recently overcome these issues and formulated an oil-in-water emulsion composed of taxine, an oil, water and a surfactant. In this formulation, a taxine such as taxol is solubilized in the oil in an effective pharmaceutical amount for intravenous administration. The taxine and oil mixture forms a dispersed phase in the water. The oil may be any of a number of oils such as mineral, vegetable, animal, essential and synthetic oils, or mixtures thereof. Preferably, the oil is rich in triglycerides, such as safflower oil, soybean oil or mixtures thereof. Because taxol is more soluble in safflower oil than soybean oil, safflower oil is most preferred. The surfactant used may be any of a number of surfactants, and usually is a phospholipid suchas lecithin. Typically, the taxine is present in an amount of about 0.1% to about 1% by weight of the emulsion, while the oil is present in an amount of from about 1% to about 40% and the surfactant is present in an amount of about 0.5% to about 5% by weight of the emulsion.

EXAMPLE 1

Preparation of Biotinylated Doxorubicin Emulsion

Targeting of doxorubicin therapeutic emulsions may be achieved with a three-step process for "pretargeting" a biotinylated antibody and subsequent binding of a biotinylated emulsion to a molecular epitope. The emulsion itself is produced by incorporating biotinylated phosphatidylethanolamine into the outer lipid monolayer of a perfluorocarbon microemulsion. Briefly, the emulsion comprises perfluorooctylbromide (40% w/v, PFOB, 3M), a surfactant co-mixture (2.0%, w/v) and glycerin (1.7%, w/v). The surfactant co-mixture includes 64 mole% lecithin (Pharmacia Inc), 35 mole% cholesterol (Sigma Chemical Co.) and 1 mole% N-(6-(biotinoyl)amino) hexanoyl)-dipalmitoyl-L-alpha-phosphatidyl-ethanolamine, Pierce Inc.) which are dissolved in chloroform. Doxorubicin is suspended in methanol (~25 µg/20 µl) and added in titrated amounts between 0.01 and 5.0 mol % of the 2% surfactant layer, preferably between 0.2 and 2.0 mol %, The chloroform-lipid mixture is evaporated under reduced pressure, dried in a 50° C. vacuum oven overnight and dispersed into water by sonication. The suspension is transferred into a blender cup (Dynamics Corporation of America) with perfluorooctylbromide and distilled, deionized water and emulsified for 30 to 60 seconds. The emulsified mixture is transferred to a Microfluidics emulsifier (Microfluidics Co.) and continuously processed at 20,000 PSI for three minutes. The completed emulsion is vialed, blanketed with nitrogen and sealed with stopper crimp seal until use. A control emulsion can be prepared identically excluding doxorubicin from the surfactant comixture. Particle sizes are determined in triplicate at 37° C. with a laser light scattering submicron particle size analyzer (Malvern Zetasizer 4, Malvern Instruments Ltd, Southborough, Mass.)., which indicate tight and highly reproducible size distribution with average diameters less than 400 nm. Unincorporated drug can be removed by dialysis or ultrafiltration techniques.

Antibody of $F_{(ab)}$ fragment prepared as descrbed below is biotinylated using the EZ-link™ Sulfo-NHS-LC-Biotinylation Kit. Briefly, 2 to 10 mg of protein in 1 ml of phosphate buffered saline is combined with Sulfo-NHS-LC-Biotin in distilled or deionized water.to afford a 12 to 20-fold molar excess of reagent to protein. Incubate solution in ce for 2 hours or at room temperature for 30 minutes. Separate biotinylated protein from reagents using a 10 ml desalting column equilibrated and eluted with phosphate buffered saline. Collect fractions of eluate and measure UV absorbance at 280 nm with a spectrophotometer. Store at 4° C. until use.

EXAMPLE 2

Preparation of Antibody [$F_{(ab)}$]-conjugated Doxorubicin Emulsion

The perfluorocarbon nanoparticle contrast agent is produced by incorporating 1,2-dipalmitoyl-sn glycero-3-phosphoethanolamine-N-4-(p-maleimidophenyl) butyramide (MPB-PE) into the outer lipid monolayer of the emulsion to accommodate ligand conjugation. The emulsion is comprised of perfluorooctylbromide (40% w/v), a surfactant co-mixture (2% w/v), glycerin (1.2% w/v) and water (54.8% w/v). The surfactant co-mixture included lecithin (67.9 mol %), cholesterol (30 mol %), dipalmitoyl-phosphatidylethanolamine (2 mol %) and MPB-PE (0.1 mol %) and is dissolved in chloroform. Doxorubicin is suspended in methanol (~25 μg/20 μl) and added in titrated amounts between 0.01 and 5.0 mol % of the 2% surfactant layer, preferably between 0.2 and 2.0 mol %. The chloroform-lipid mixture is evaporated under reduced pressure, dried in a 50° C. vacuum oven overnight and dispersed into water by sonication. The suspension is transferred into a blender cup with perfluorocarbon, safflower oil and distilled, deionized water and emulsified as above. A control emulsion is prepared identically except a nonderivatized phosphatidylethanolamine may be substituted into the surfactant co-mixture. The completed emulsion is vialed, blanketed with nitrogen and sealed with stopper crimp seal until use. A control emulsion can be prepared identically excluding doxorubicin from the surfactant comixture. Particle sizes are determined in triplicate at 37° C. with a laser light scattering submicron particle size analyzer (Malvern Zetasizer 4, Malvern Instruments Ltd, Southborough, Mass.) ., which indicate tight and highly reproducible size distribution with average diameters less than 400 nm. Unincorporated drug is removed by dialysis.

F(ab)' fragments are generated and isolated using an immunopure F(ab)' preparation kit (Pierce, Rockford, Ill.). Briefly, IgG is dialyzed into 20 mM phosphate/10 mM EDTA buffer (pH 7.0), concentrated to 20 mg/ml and digested by immobilized papain. Solubilized F(ab)' is purified from Fc fragments and undigested IgG protein using a protein A column. F(ab)' fragments is purified from excess cysteine using a G25-150 column and deoxygenated phosphate buffer (pH 6.7). Fraction identity is confirmed by routine SDS-PAGE procedures. An analogous emulsion using an irrelevant IgG is used to prepare control ligands with random specificities.

F(ab)' fractions are pooled and combined with the MPB-PE derivatized emulsion (1–2 mg F(ab)'/ml of emulsion). The mixture is adjusted to pH 6.7, sealed under nitrogen and allowed to react overnight at ambient temperatures with gentle, continuous mixing. The mixture is subsequently dialyzed with a 300,000 MWCO Spectra/Por DispoDialyzer (Laguna Hills, Calif.) against 10 mM phosphate buffer (pH 7.2) to remove unconjugated F(ab)' fragments. The final emulsion is vialed under nitrogen and stored at 4° C. until use. A nonspecific control emulsion may be prepared using the control, irrelevant IgG F(ab)' fragments in the above protocol.

EXAMPLE 3

Effectiveness of Therapeutic Doxorubicin (DXR) Nanoparticle Emulsions Targeted to Tissue Factor on Porcine Aortic Smooth Muscle Cells Example 3 demonstrates the enhanced efficacy of ligand-targeted doxorubicin nanoparticle emulsions versus free doxorubicon to inhibit the proliferation of aortic smooth muscle cells in vitro. Pig aortic smooth muscle cells are seeded onto 12mm round glass coverslips in 24 well cluster plates at a density of $5 \times 10^4$ cells per well (n=45; 9/treatment). The cells are grown in smooth muscle basal medium containing 5% FBS for 72 hours, then rinsed in media and incubated on a platform shaker at 37° C., 95%/5% O/CO2 with medium containing biotinylated anti-tissue factor antibody (25 μg) for 1 hour. Excess antibody is rinsed from cultures 3×. Cells are next incubated with 25 μg of avidin (Pierce, Rockford, Ill.) for 30 min then washed 3× to remove excess avidin. Finally, doxorubicin emulsion (25 μl) incorporating 0, 0.2 or 2.0 mol % drug within the phospholipid surfactant, is incubated with the cells for 30 minutes at 37° C. The cells were washed free of unbound emulsion or drug 3× and allowed to continue growing at 37° C., 95%/5% O/CO2. After 48 hours additional growth, the cells were dispersed from the cover slips with trypsin and counted with a hemacytometer (FIG. 1).

Tissue factor-targeted DXR nanoparticles had greater anti-proliferative effects than the free doxorubicin and this differential effect was greater at the lower dosage of DXR. DXR nanoparticles decreased cell proliferation in a dose responsive manner. The results suggest that DXR formulated into the lipid surfactant was retained and slowly delivered from the nanoparticles into the smooth muscle cells. The delivery of DXR into the pig aortic smooth muscle cells is facilitated by the intimate, prolonged contact of the emulsion nanoparticles with the cell membrane surface and exchange of lipids and drug between the two lipid layers.

EXAMPLE 4

Figure 2:
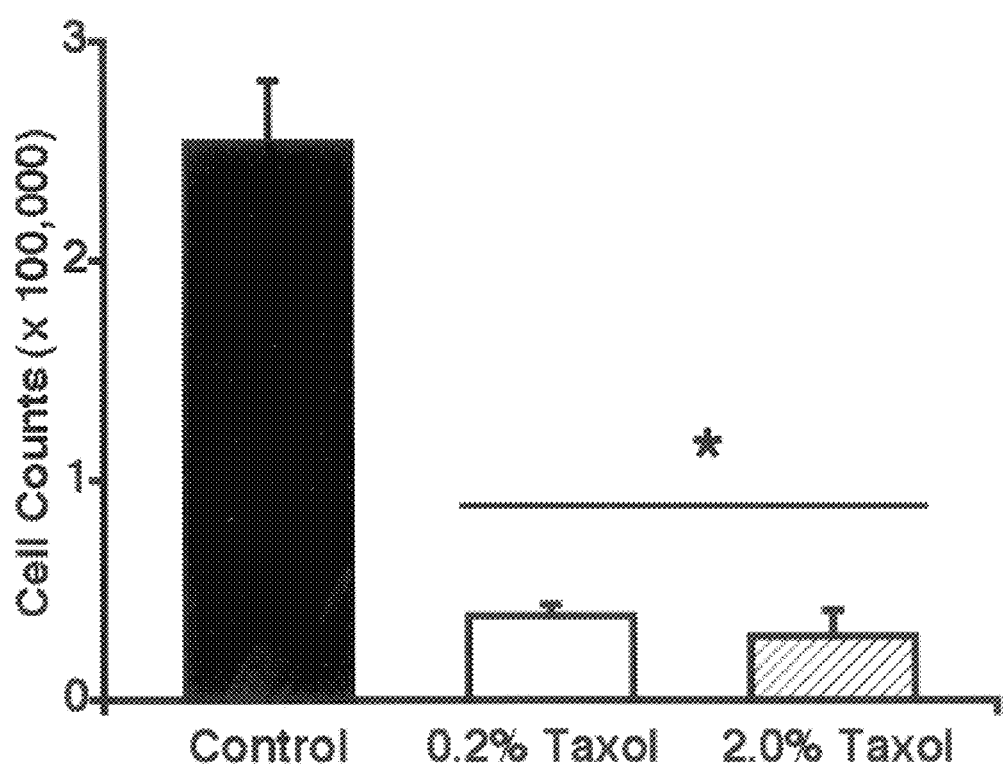
FIG. 2 is a graph showing the effectiveness of therapeutic paclitaxel (Taxol) nanoparticle emulsions targeted to tissue factor on porcine aortic smooth muscle cells in accordance with the present invention.

Effectiveness of Therapeutic Paclitaxel (Taxol) Nanoparticle Emulsions Targeted to Tissue Factor on Porcine Aortic Smooth Muscle Cells Example 4 demonstrates the efficacy of ligand-targeted paclitaxel nanoparticle emulsions versus a targeted-control emulsion to inhibit the proliferation of aortic smooth muscle cells in vitro. Since paclitaxel is highly insoluble in buffer, comparisons of nanoparticle formulations with free drug were not possible. Pig aortic smooth muscle cells were seeded onto 12 mm round glass cover slips in 24 well cluster plates at a density of $5 \times 10^4$ cells per well (n=18; 6/treatment). The cells were grown in smooth muscle basal medium containing 5% FBS for 72 hours, then rinsed in media and incubated on a platform shaker at 37° C., 95%/5% O/CO2 with medium containing biotinylated anti-tissue factor antibody (25 μg) for 1 hour. Excess antibody was rinsed from cultures 3×. Cells were next incubated with 25 μg of avidin (Pierce, Rockford, Ill.) for 30 min then washed 3× to remove excess avidin. Finally, paclitaxel emulsions (25 μl) at concentrations of 0, 0.2 and 2.0 mol % within the phospholipid surfactant, were incubated with the cell cultures for 30 minutes at 37° C. The cells were washed free of unbound emulsion (i.e. 3 rinses) and allowed to grow at 37° C., 95%/5% O/CO2. After 48 hours, the cells were trypsinized and counted with a hemacytometer (FIG. 2).

Tissue factor-targeted paclitaxel nanoparticles had marked, equivalent anti-proliferative effects at both dosages of paclitaxel. Paclitaxel, although highly insoluble in aqueous culture medium, was effectively delivered and inhibited the proliferation of aortic smooth muscle cells. These results suggest that paclitaxel formulated into the lipid surfactant was delivered from the nanoparticles directly into the smooth muscle cell membrane. The delivery of paclitaxel to the pig aortic smooth muscle cells was facilitated by the intimate, prolonged contact of the emulsion nanoparticles with the cell membrane surface and exchange of lipids and drug between the two lipid layers.

EXAMPLE 5

Enhanced Effectiveness of Therapeutic Doxorubicin or Paclitaxel Nanoparticle Emulsions Targeted to Tissue Factor on Porcine Aortic Smooth Muscle Cells Example 5 demonstrates the enhanced effectiveness of ligand-targeted doxorubicin or paclitaxel nanoparticle emulsions versus non-targeted nanoparticle emulsion. This example illustrates the importance of ligand-targeting versus free emulsions. Pig aortic smooth muscle cells were seeded onto 12 mm round glass cover slips in 24 well cluster plates at a density of $5 \times 10^4$ cells per well (n=30; 3/treatment). The cells were grown in smooth muscle basal medium containing 5% FBS for 72 hours, then rinsed in media and incubated on a platform shaker at 37° C., 95%/5% O/CO2 with medium. One half of the wells received biotinylated anti-tissue factor antibody (25 μg) for 1 hour. Excess antibody and media was rinsed from all cultures 3x. One half of the cells were next incubated with 25 μg of avidin (Pierce, Rockford, Ill.) for 30 min then washed 3x to remove excess avidin and media. Finally, paclitaxel, doxorubicin or control (no drug) emulsions (25 μl) at drug concentrations of 0, 0.2 and 2.0 mol % within the phospholipid surfactant, were incubated with the cell cultures for 30 minutes at 37° C. The cells were washed free of unbound emulsion (i.e. 3 rinses) and allowed to grow at 37° C., 95%/5% O/CO2. After 48 hours, the cells were trypsinized and counted with a hemacytometer (Table 1).

TABLE 1

The effect of targeted and free therapeutic nanoparticles on porcine aortic cell proliferation (cell counts × 10,000) in vitro.

| | | Doxorubicin (DXR) | | Paclitaxel (Taxol) | |
|---|---|---|---|---|---|
| Antibody | Control | 0.2 mol % | 2.0 mol % | 0.2 mol % | 2.0 mol % |
| Free | 23.3 ± 1.8$^a$ | 12.7 ± 1.0$^b$ | 7.9 ± 0.3$^c$ | 25.0 ± 1.5$^a$ | 23.0 ± 1.5$^a$ |
| Targeted | 27.0 ± 1.2$^a$ | 6.0 ± 1.9$^c$ | 1.9 ± 0.7$^d$ | 7.0 ± 0.6$^c$ | 5.2 ± 0.4$^c$ |

$^{abc}$Means (± std error) with different superscripts are significantly different ($p < 0.05$).

Figure 3:
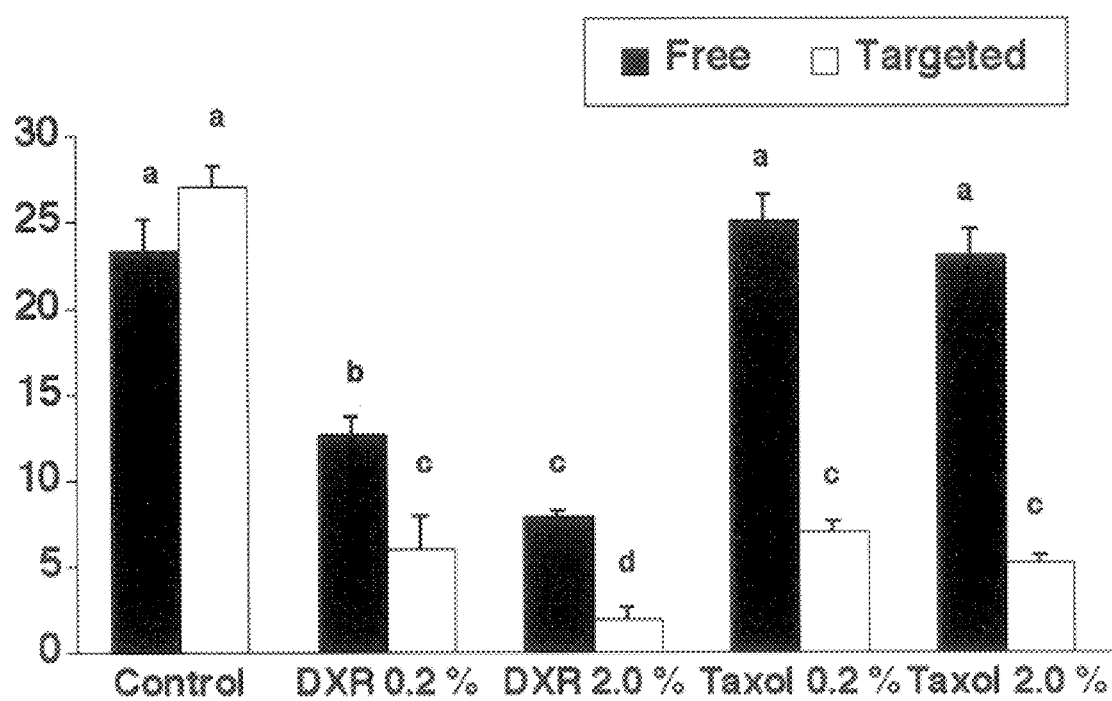
FIG. 3 is a graph showing the enhanced effectiveness of therapeutic doxorubicin (DXR) or paclitaxel (Taxol) nanoparticle emulsions targeted to tissue factor on porcine aortic smooth muscle cells.

Tissue factor-targeted nanoparticles had greater antiproliferative effects at both dosages of paclitaxel or doxorubicin than free therapeutic emulsion. The greatest benefit was measured for paclitaxel, the most hydrophobic compound. The control emulsions, free or targeted did not inhibit cell proliferation. Free paclitaxel emulsion nanoparticles did not affect cell growth regardless of dosage. Free doxorubicin emulsion particles did inhibit cell growth in a dose related fashion, but the effect was most pronounced when the particles were actively targeted to the cell surface with anti-tissue factor antibody, an epitope constitutively expressed by these cells. The delivery of paclitaxel or doxorubicin into the pig aortic smooth muscle cells was facilitated by the intimate, prolonged contact of the emulsion nanoparticles with the cell membrane surface and the exchange of lipids and drug between the two lipid layers (see FIG. 3).

As various changes could be made in the above methods and compositions without departing from the scope of the invention, it is intended that all matter contained in the above description and shown in the accompanying drawings shall be interpreted as illustrative and not in a limiting sense.

What is claimed is:

1. A composition for use in delivering a bioactive agent to targeted tissues or cells comprising:
   (a) a lipid-encapsulated oil in water emulsion of fluorochemical particles, wherein the particles have an outer monolayer of lipid and wherein the lipid outer monolayer further comprises a primer material;
   (b) a bioactive agent in or on the surface of the lipid outer monolayer of the particles; and
   (c) a site-specific targeting ligand, wherein the ligand is covalently coupled to the primer material;

wherein the primer material is selected from the group consisting of 1-ethyl-3-(3-N-N-dimethylaminopropyl) carbodiimide hydrochloride, 1-cyclohexyl-3-(2-morpholinoethyl)carbodiimide methyl-p-toluenesulfonate, and 1,2-diacyl-sn-glycerol-3-phosphoethanolamine-N-(4-p-maleimidephenyl)-butyramide.

2. A composition as set forth in claim 1 wherein said site-specific targeting ligand is selected from the group consisting of antibodies, antibody fragments, peptides, asialoglycoproteins, polysaccharides, aptamers, nucleic acids, peptidomimetics, mimetics and drugs.

3. A composition as set forth in claim 2 wherein said site-specific targeting ligand is an antibody.

4. A composition as set forth in claim 1 wherein said fluorochemical is a fluorocarbon.

5. A composition as set forth in claim 4 wherein said fluorocarbon is perfluorooctylbromide.

6. A composition as set forth in claim 1 wherein said fluorochemical is a liquid with a boiling point above approximately 30° C.

7. A composition as set forth in claim 6 wherein said fluorochemical liquid has a boiling point above approximately 90° C.

8. A composition as set forth in claim 1 wherein said bioactive agent is selected from the group consisting of chemotherapeutic agents, drugs, genetic materials, nucleic acid-based therapy, protein or peptide therapy, radioactive isotopes or combinations thereof.

9. A composition as set forth in claim 8 wherein said bioactive agent is a chemotherapeutic agent.

10. A composition as set forth in claim 1 wherein said lipid outer monolayer is composed of a material selected from the group consisting of a natural or synthetic phospholipid, a fatty acid, cholesterol, lysolipid, sphingomyelin, tocopherol, glucolipid, stearylamine, cardiolipin, a lipid with ether or ester linked fatty acids and a polymerized lipid.

11. A composition as set forth in claim 1 wherein said lipid outer monolayer also contains an additional surfactant incorporated therein for stabilizing said emulsion.

12. A composition as set forth in claim 11 wherein said additional surfactant is selected from the group consisting of nonionic and amphoteric surfactants.

13. A composition as set forth in claim 11 wherein said surfactant contains a cationic lipid to facilitate adhesion of said bioactive agent to said emulsion particles.

14. A composition as set forth in claim 13 wherein said cationic lipid is selected from the group consisting of N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethylammonio)butanoyl-sn-glycerol, 1,2-diacyl-3-trimethylammonium-propane, 1,2-diacyl-3-dimethylammonium-propane, and 3β-[N',N'-dimethylaminoethane)-carbamol]cholesterol-HCl.

15. A composition as set forth in claim 1 wherein said emulsion contains an emulsifying and/or solubilizing agent.

16. A composition as set forth in claim 1 wherein said emulsion particles have a diameter in the range of approximately 0.01 to 10 microns.

17. A composition as set forth in claim 16 wherein said emulsion particles have a diameter in the range of approximately 0.1 to 0.5 microns.

18. A composition for use in delivering a bioactive agent to targeted tissues or cells comprising:
   (a) a lipid-encapsulated oil in water emulsion of fluorochemical particles, wherein the particles have an outer monolayer of lipid and wherein the lipid outer monolayer further comprises a primer material; and (b) a combination site-specific targeting ligand/bioactive agent in or on the surface of the lipid outer monolayer of the particles; wherein said combination ligand/bioactive agent is covalently coupled to the primer material; wherein the primer material is selected from the group consisting of 1-ethyl-3-(3-N-N-dimethylaminopropyl)carbodiimide hydrochloride, 1-cyclohexyl-3-(2-morpholinoethyl)carbodiimide methyl-p-toluenesulfonate, and 1,2-diacyl-sn-glycerol-3-phosphoethanolamine-N-(4-p-maleimidephenyl)-butyramide.

19. A composition as set forth in claim 18 wherein said combination ligand/bioactive agent is selected from the group consisting of antibodies, antibody fragments, peptides and mimetics.

20. A composition as set forth in claim 19 wherein said combination ligand/bioactive agent is an antibody.

21. A composition as set forth in claim 18 wherein said fluorochemical is a fluorocarbon.

22. A composition as set forth in claim 18 wherein said fluorochemical is a liquid with a boiling point above approximately 30° C.

23. A composition as set forth in claim 22 wherein said fluorochemical liquid has a boiling point above approximately 90° C.

24. A composition as set forth in claim 18 wherein said lipid outer monolayer is composed of a material selected form the group consisting of a natural or synthetic phospholipid, a fatty acid, cholesterol, lysolipid, sphingomyelin, tocopherol, glucolipid, stearylamine, cardiolipin, a lipid with ether or ester linked fatty acids and a polymerized lipid.

25. A composition as set forth in claim 18 wherein said lipid outer monolayer also contains an additional surfactant incorporated therein for stabilizing said emulsion.

26. A composition as set forth in claim 25 wherein said surfactant contains a cationic lipid to facilitate adhesion of said ligand/bioactive agent to said emulsion particles.

27. A composition as set forth in claim 18 wherein said emulsion contains an emulsifying agent and/or solubilizing agent.

28. A composition as set forth in claim 18 wherein said emulsion particles have a diameter in the range of approximately 0.10 to 10 microns.

29. A composition as set forth in claim 28 wherein said emulsion particles have a diameter in the range of approximately 0.1 to 0.5 microns.

30. A method for improved delivery of a bioactive agent to targeted tissues or cells comprising administering to said tissues or cells a composition comprising:

(a) a lipid-encapsulated oil in water emulsion of fluorochemical particles, wherein the particles have an outer monolayer of lipid and wherein the lipid outer monolayer further comprises a primer material;

(b) a bioactive agent in or on the surface of the lipid outer monolayer of the particles; and (c) a site-specific targeting ligand, wherein the ligand is covalently coupled to the primer material;

wherein the primer material is selected from the group consisting of 1-ethyl-3-(3-N-N-dimethylaminopropyl) carbodiimide hydrochloride, 1-cyclohexyl-3-(2-morpholinoethyl)carbodiimide methyl-p-toluenesulfonate, and 1,2-diacyl-sn-glycerol-3-phosphoethanolamine-N-(4-p-maleimidephenyl)-butyramide.

31. A method as set forth in claim 30 wherein said site-specific targeting ligand is selected from the group consisting of antibodies, antibody fragments, peptides, asialoglycoproteins, polysaccharides, aptamers, nucleic acids, peptidomimetics, mimetics and drugs.

32. A method as set forth in claim 31 wherein said site-specific targeting ligand is an antibody.

33. A method as set forth in claim 30 wherein said fluorochemical is a fluorocarbon.

34. A method as set forth in claim 33 wherein said fluorocarbon is perfluorooctylbromide.

35. A method as set forth in claim 30 wherein said fluorochemical is a liquid with a boiling point above approximately 30° C.

36. A method as set forth in claim 35 wherein said fluorochemical liquid has a boiling point above approximately 90° C.

37. A method as set forth in claim 30 wherein said bioactive agent is selected from the group consisting of chemotherapeutic agents, drugs, genetic materials, nucleic acid-based therapy, protein or peptide therapy, radioactive isotopes or combinations thereof.

38. A method as set forth in claim 37 wherein said bioactive agent is a chemotherapeutic agent.

39. A method as set forth in claim 30 wherein said lipid outer monolayer is composed of a material selected from the group consisting of a natural or synthetic phospholipid, a fatty acid, cholesterol, lysolipid, sphingomyelin, tocopherol, glucolipid, stearylamine, cardiolipin, a lipid with ether or ester linked fatty acids and a polymerized lipid.

40. A method as set forth in claim 30 wherein said lipid outer monolayer also contains an additional surfactant incorporated thereon for stabilizing said emulsion.

41. A method as set forth in claim 40 wherein said additional surfactant is selected from the group consisting of nonionic and amphoteric surfactants.

42. A method as set forth in claim 40 wherein said surfactant contains a cationic lipid to facilitate adhesion of said bioactive agent to said emulsion particles.

43. A method as set forth in claim 30 wherein said emulsion contains an emulsifying and/or solubilizing agent.

44. A method as set forth in claim 30 wherein said emulsion particles have a diameter in the range of approximately 0.01 to 10 microns.

45. A method as set forth in claim 44 wherein said emulsion particles have a diameter in the range of approximately 0.1 to 0.5 microns.

46. A method for improved delivery of a bioactive agent to targeted tissues or cells comprising administering to said tissues or cells a composition comprising:

(a) a lipid-encapsulated oil in water emulsion of fluorochemical particles, wherein the particles have an outer monolayer of lipid and wherein the lipid outer monolayer further comprises a primer material; and (b) a combination site-specific targeting ligand/bioactive agent in or on the surface of the lipid outer monolayer of the particles; wherein said combination ligand/bioactive agent is covalently coupled to the primer material; wherein the primer material is selected from the group consisting of 1-ethyl-3-(3-N-N-dimethylaminopropyl)carbodiimide hydrochloride, 1-cyclohexyl-3-(2-morpholinoethyl)carbodiimide methyl-p-toluenesulfonate, and 1,2-diacyl-sn-glycerol-3-phosphoethanolamine-N-(4-p-maleimidephenyl)-butyramide.

47. A method as set forth in claim 46 wherein said combination ligand/bioactive agent is selected from the group consisting of antibodies, antibody fragments, peptides, and mimetics.

48. A method as set forth in claim 47 wherein said combination ligand/bioactive agent is an antibody.

49. A method as set forth in claim 46 wherein said fluorochemical is a fluorocarbon.

50. A method as set forth in claim 46 wherein said fluorochemical is a liquid with a boiling point above approximately 30° C.

51. A method as set forth in claim 50 wherein said fluorochemical liquid has a boiling point above approximately 90° C.

52. A method as set forth in claim 46 wherein said lipid outer monolayer is composed of a material selected from the group consisting of a natural or synthetic phospholipid, a fatty acid, cholesterol, lysolipid, sphingomyelin, tocopherol, glucolipid, stearylamine, cardiolipin, a lipid with ether or ester linked fatty acids and a polymerized lipid.

53. A method as set forth in claim 46 wherein said lipid outer monolayer also contains an additional surfactant incorporated therein for stabilizing said emulsion.

54. A method as set forth in claim 53 wherein said surfactant contains a cationic lipid to facilitate adhesion of said ligand/bioactive agent to said emulsion particles.

55. A method as set forth in claim 46 wherein said emulsion contains an emulsifying agent and/or solubilizing agent.

56. A method as set forth in claim 46 wherein said emulsion particles have a diameter in the range of approximately 0.01 to 10 microns.

57. A method as set forth in claim 56 wherein said emulsion particles have a diameter in the range of approximately 0.1 to 0.5 microns.

58. A composition as set forth in claim 26 wherein said cationic lipid is selected from the group consisting of N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethylammonio)butanoyl-sn-glycerol, 1,2-diacyl-3-trimethylammonium-propane, 1,2-diacyl-3-dimethylammonium-propane, and 3β-[N',N'-dimethylaminoethane-carbamol]cholesterol-HCl.

59. A method as set forth in claim 42 wherein said cationic lipid is selected from the group consisting of N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethylammonio)butanoyl-sn-glycerol, 1,2-diacyl-3-trimethylammonium-propane, 1,2-diacyl-3-dimethylammonium-propane, and 3β-[N',N'-dimethylaminoethane-carbamol]cholesterol-HCl.

60. A method as set forth in claim 54 wherein said cationic lipid is selected from the group consisting of N-[1-(2,3-dioleoyloxy)propyl]-N,N,N-trimethylammonium chloride, 1,2-dioleoyloxy-3-(trimethylammonio)propane, 1,2-dioleoyl-3-(4'-trimethylammonio)butanoyl-sn-glycerol, 1,2-diacyl-3-trimethylammonium-propane, 1,2-diacyl-3-dimethylammonium-propane, and 3β-[N',N'-dimethylaminoethane-carbamol]cholesterol-HCl.

\* \* \* \* \*